United States Patent [19]

Chao

[11] 3,947,605
[45] Mar. 30, 1976

[54] PROCESS FOR PREPARING HIGH YIELDS OF SINGLE CELL PRODUCTS HAVING REDUCED PURINE CONTENT AND HIGH NUTRITIVE VALUE

[75] Inventor: Kwei C. Chao, Naperville, Ill.

[73] Assignee: Standard Oil Company, Chicago, Ill.

[22] Filed: Oct. 30, 1974

[21] Appl. No.: 519,265

[52] U.S. Cl................ 426/656; 426/60; 260/112 R
[51] Int. Cl.$^2$............................................ A23J 1/00
[58] Field of Search...................... 426/204, 60, 656; 260/112 R; 195/28 R, 28 N

[56] References Cited
UNITED STATES PATENTS

| | | | |
|---|---|---|---|
| 3,775,393 | 11/1973 | Akin et al. | 260/112 R |
| 3,809,776 | 5/1974 | Chao | 426/204 X |
| 3,867,555 | 2/1975 | Newell et al. | 426/204 X |

*Primary Examiner*—A. Louis Monacell
*Assistant Examiner*—R. B. Penland
*Attorney, Agent, or Firm*—Werten F. W. Bellamy; Arthur G. Gilkes; William T. McClain

[57] ABSTRACT

Single-cell protein material, having low purine content and high nutritive value, is obtained in high yield by subjecting aqueous cell creams to temperature, pH adjustment, and washing treatments for controlled periods of time. This process can involve methionine or cystine enrichment of the products produced thereby.

18 Claims, No Drawings

PROCESS FOR PREPARING HIGH YIELDS OF SINGLE CELL PRODUCTS HAVING REDUCED PURINE CONTENT AND HIGH NUTRITIVE VALUE

BACKGROUND OF THE INVENTION

In recent years much attention has been directed toward the development of new sources of protein for human consumption. There exists a need for protein material which can be incorporated in foods or usable as a basic proteinaceous substance for human consumption. Rapid increases in world population have made the continued dependence on traditional sources of protein highly impractical. Moreover, the supply of protein from typical sources of protein, such as animal meat and certain vegetables, is inadequate to provide balanced diets sufficient to satisfy needs of humans throughout the world. These factors coupled with the difficulties associated with providing protein from traditional sources because of drought, flooding and both animal and crop diseases gives critical significance to this situation.

One possible solution to the problem of supplying the ever increasing need for food protein is provided by processes for the bio-synthetic manufacture of protein through the growth of microorganisms on hydrocarbon or other substrates. It is known, for example, that microorganisms such as fungi, bacteria and yeast, which are grown by single-cell reproduction, contain high proportions of proteins and can be utilized directly in foods as wholecell material or can be treated to recover protein isolate. Recent efforts have shown that microorganisms, grown on hydrocarbon substrates can be successfully used in animal feeds; but as yet these microorganisms have not been commercially accepted in food preparations suitable for human consumption.

With the development of successful processes for the synthetic production of protein-containing microorganisms (sometimes referred to herein as single cell proteins), an urgent need has developed for methods of texturizing such single-cell protein materials in a manner sufficient to render them suitable for use in food products. Generally, single-cell protein is initially produced as a wet paste and then is subsequently converted into dry powder form. This dry powder, similar in appearance and feel to flour, lacks the texture and food-like sensation to the mouth necessary to make an attractive food. Moreover, when placed in water, the powdered single-cell protein rapidly reverts back to single-cell form.

Ideally, therefore, it is desirable to impart properties such as chewiness, crispness, resistance to dispersion in water and the like to such single-cell proteins in order that they may be used to full advantage as additives to and substitutes for natural foods.

Various techniques are known in the art for effecting texture formation in soy bean based protein, such techniques are not generally applicable to single-cell technology and are ineffective in such application.

The use of "texturized vegetable proteins" (hereinafter referred to as TVP) in food products, especially as meat extenders or analogs has been increasing rapidly. Many people predict that the market for TVP may reach 10% of all domestic meat consumption by the year 1985. The technology of texturizing soy protein is well established. Presently, there are mainly two types of TVP produced on the market. Namely, the expanded vegetable protein is made by a thermoplastic extrusion technique and the spun vegetable protein by a fiber spinning technique. TVP is characacterized as having structural integrity and identifiable texture. These features enable it to withstand hydration in cooking and other procedures used in preparing the food.

In order for single-cell proteins (SCP) to compete with vegetable seed proteins and to share the protein market in the future, it has to be texturized and processed for the removal of purine.

The human metabolic system produces uric acid as in the metabolism of purine. Since man does not have a uricase enzyme system, uric acid is not further broken down and is excreted with urine. Because uric acid has a very low solubility in water it will accumulate in the body in crystalline form if produced in larger quantities than the body can excrete. This may lead to the conditions known as gout and kidney stone formation. It is, therefore, recommended by many nutritionists that the purine intake in diet be kept at a low level.

Microbial cells, or single-cell protein (SCP) materials, contain from 4 to 30% or more nucleic acids according to their growth rates and the phase of growth. Usually, the higher nucleic acid contents of the microbial cells are associated with rapid growth phases. If the microbial cells are to be used as a protein source in human feeding, nutritionists recommend generally that the amount of nucleic acids contributed by SCP to diet should not exceed 2 grams per day which is equivalent to 0.36 grams of purine bases.

The calculated ribonucleic acid (RNA) contents of some conventional protein sources are given in Table I. These vary from 0 to 4%. The RNA content of SCP generally ranges from 8 to 18% for exponential growth phase cells. In SCP intended for human consumption the RNA content should preferably be reduced to about 2% on cell dry weight basis. Again, the level of 2% RNA on a cell dry weight basis is equivalent to 0.36 grams of purine bases.

TABLE I

| RNA Content (Calculated) of Various Protein Sources | |
|---|---|
| FOOD | % RNA |
| Milk | 0 |
| Beans | 1.7 |
| Salmon | 2.4 |
| Chicken | 2.9 |
| Beef | 3.7 |
| Pork | 4.1 |
| Liver | 9.3 |
| Anchovies | 14.5 |
| SCP | 8 to 18 |

A preferred way of utilizing SCP material is in the form of whole cells. In this form, there is a need for the development of means for removing nucleic acids from the microbial cell material. This is desirably accomplished with a minimum loss of protein materials from the cells in order to maintain the nutritional attractiveness of such SCP materials.

SUMMARY OF THE INVENTION

The present invention is directed to a two-step extraction process for substantially reducing the purine content of single-cell proteins. It has been found that nutritive materials such as B-vitamins, amino acids, peptides and proteins, carbohydrates, nucleotidic material and minerals are extracted from the yeast cells by hot water having a temperature of about 70° to about 90°C. The extraction process is carried out over a period of about five to about ten minutes. The cells are separated and treated by a second extraction where the cells are extracted at a temperature of about 85° to 95°C with a dilute alkali solution having a pH of about 8.5 to about 10.0 for a period of from about 5 to about 30 minutes. The alkali-extracted cells contain very low purine content of less than 0.3% by weight. These low purine containing cells can be combined with varying amounts of the water soluble materials obtained from the first extraction step resulting in a reconstituted product. The reconstituted product will contain a low purine content ranging from 0.3 to 0.7% as compared to a level of 1.8 to 2.0% existing in untreated cells. The yield of the reconstituted product can be as high as 90% based on the weight of the starting cell material. When the alkali-extracted fraction is not reconstituted in the manner above mentioned, the yield will be about 72%.

Optimally, both the reconstituted product and alkali-extracted fraction can be fortified with a nutrient such as methionine or cystine.

DESCRIPTION OF PREFERRED EMBODIMENTS

This invention discloses a novel method for reducing the purine content of unicellular microorganisms together with the novel and improved food products obtained thereby.

It has been found that the purine content of single-cell microorganisms can be reduced in accordance with the two step extraction process as outlined in FIG. 1. The steps involved in this process are as follows:

1. Yeast cream in a concentration of 10 to 14 wt.% is heated to 70° to 90°C. through a heat exchanger for a residence time of about 5 to about 10 minutes;

2. the heated cell suspension is cooled down rapidly to the room temperature and the cells are separated and washed by centrifugation into cell concentrate;

3. the supernatant (Extract-1) is to be directly reconstituted into the final product, or sent to the zone wherein purine related substances are removed by any effective method of fractionation;

4. the washed cell concentrate from step (2) is resuspended in water to produce a cell suspension of 10 to 14 wt.% (dry basis);

5. a base solution such as NaOH, NH$_4$OH or NaCO$_3$ is added to the suspension of step (4) in order to raise the pH level to about 8.5 to about 10.0 (e.g. the amount of NaOH added corresponds to 0.7 to 1.6% of cell (dry basis));

6. the cell suspension is then heated to about 85° to about 95°C. through a heat exchanger for a residence time of about 5 to about 30 minutes;

7. the heated suspension is cooled rapidly to room temperature before subjecting it to centrifugation;

8. the alkali-extracted cells, having low purine content, are water-washed, neutralized (to pH 7.0) and separated into a cell concentrate;

9. the alkaline supernatant (Extract-2) is sent for further processing into by-product; and 10. the cell concentrate of step (8) is directly dried into product of low purine content, or combined with varying amounts of extract (Extract-1) from step (3) to produce dried reconstituted products containing low levels of purine.

Optimally, in step (10), an additive such as methionine or cystine can be incorporated into the product to further improve its nutritive value.

It has thus been possible, by application of this inventive process, to obtain single-cell protein material in the form of intact cells and having a nucleic acid content substantially below 2 wt.% which is equivalent to 0.36 grams of purine bases.

The novel process offers the advantage of being able to prepare "tailor-made" products having desirable levels of purine. This is easily accomplished by varying the amount of Extract-1 in the reconstitution step during drying. Obviously, it costs more to produce products containing lower levels of purine because of the lower yields. However, this process affords the distinct advantage of being able to make "whole families" (closely related) of low purine containing products based on different purine content which can be used for various food applications.

The practice of this invention is broadly applicable to microorganisms and particularly to those organisms classified as bacteria, yeast and fungi. By way of illustration bacteria such as those listed in Table II, yeast such as those listed Table III and fungi such as those listed in Table IV are suitable microorganisms.

TABLE II — Suitable Bacteria

Acetobacter sp.
Arthrobacter sp.
*Bacillus subtilis*
Corynebacteria sp.
Micrococcus sp.
Pseudomonas sp.

TABLE III — Suitable Yeasts

*Candida curvata*
*Candida lipolytica*
*Candida pulcherima*
*Candida utilis*
*Hansenula anomala*
*Hansenula miso*
*Oidium lactis*
*Saccharomyces carlsbergensis*
*Saccharomyces fragilis*
*Trichosporon cutaneum*
*Saccharomyces cerevisiae*
*Candida parapsilosis*
*Hansenula wickerhamii*
*Pichia pastoris*
*Pichia haplophyla*

TABLE IV

| Suitable Fungi | |
|---|---|
| Aspergillus niger | Penicillium notatum |
| Aspergillus glaucus | Penicillium chrysogenum |
| Aspergillus oryzae | Penicillium glaucum |
| Aspergillus terreus | Penicillium griseofulvum |
| Aspergillus itaconicus | |

*Candida utilis, Saccharomyces cerevisiae, Saccharomyces fragilis,* and *Saccharomyces carlsbergensis* are preferred starting materials for the process of this invention, however, because each has been generally regarded by the F.D.A. as safe for use in food products.

Microbial cells suitable for the process of this invention may be grown aerobically in either a batch or continuous manner. Any suitable carbon-affording substrate may be employed although, for purposes of preparing SCP products for use in foods, an ethanol substrate is preferred. Any conventional combination of mineral nutrient elements may be employed. A convenient source of nitrogen is ammonia which may also be supplied to the fermentor as required to maintain the pH of the fermentation broth, preferably within the range from 3.5 to 5.5. Cells which have been grown at a rapid rate usually have a higher nucleic acid content while those grown more slowly tend to have a more permeable cell wall. Either of these types, as well as cells grown under oxygen-limiting or substrate-limiting conditions may be usefully treated according to the present invention to afford improved and acceptable foods and food components suitable for human consumption.

The following schematic diagram serves to illustrate the steps involved in the practice of this invention.

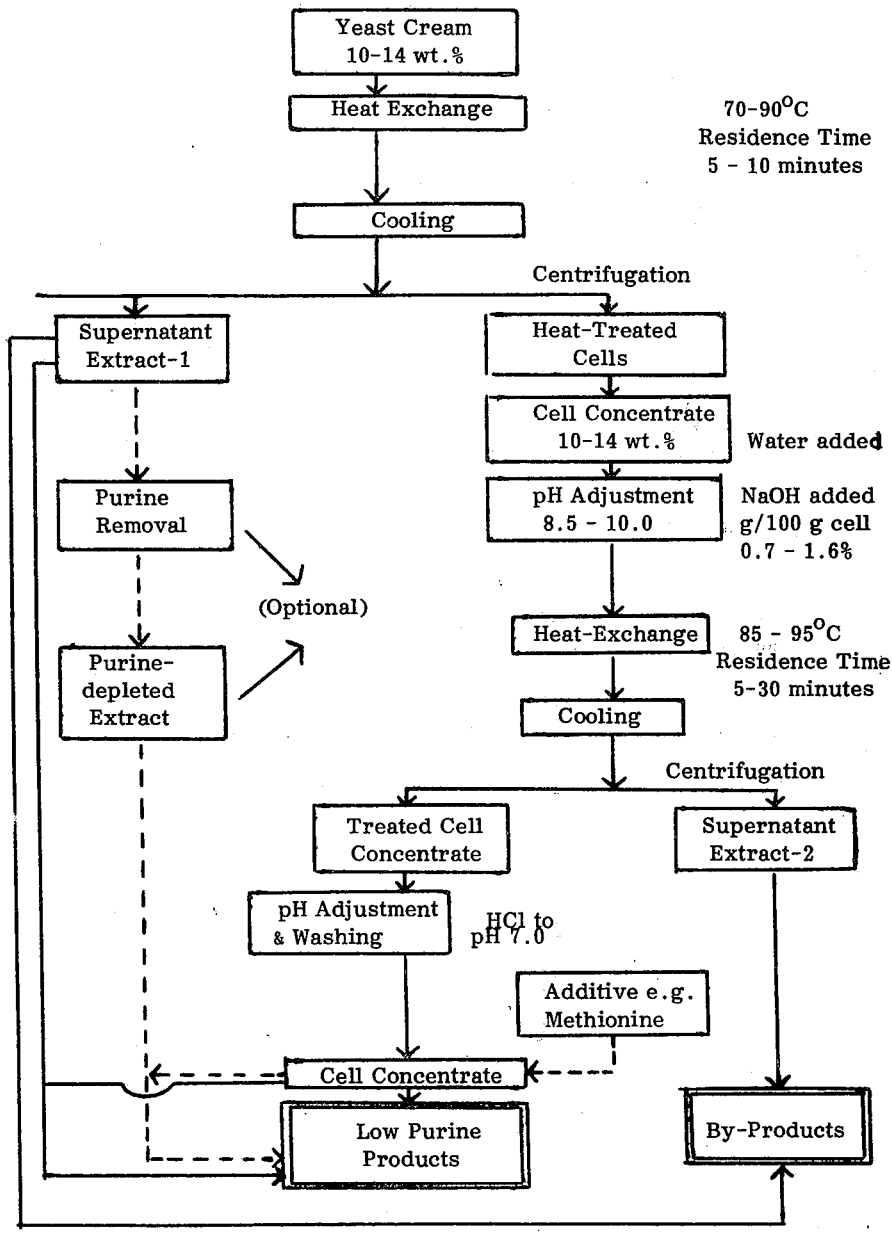

EXAMPLES

The following examples are illustrative, without implied limitation, of my invention.

EXAMPLE I

Yeast cells, *Candida utilis* (ATCC-9256), were harvested from a continuous culture which was grown on ethanol under conditions wherein the cell growth was limited by oxygen. A yeast cream containing 10 wt.% yeast cells in aqueous ethanol was prepared. The yeast cream was heated rapidly to 80°C. and maintained at that temperature for 5 minutes. The heated yeast cream was cooled rapidly to room temperature and subjected to centrifugation thereby separating the fraction (Extract-1) from the cell mass. The treated cells were mixed with water and formed an aqueous suspension containing 10 to 14 wt.% yeast cells. A 10% solution of sodium hydroxide (NaOH) was added to the aqueous cell suspension raising the pH to 9.5. The amount of NaOH used was equivalent to 1.3% of the cell dry weight. The aqueous cell suspension, containing dilute alkali, was heated rapidly to 90°C. and maintained at that temperature for 10 minutes before being cooled rapidly to room temperature. The treated cell was separated and again suspended in water thereby forming an aqueous cell suspension having a cell concentration of 10 to 14 wt.%. The pH of the cell suspension was adjusted to 7.0 by the addition of six normal hydrochloric acid (HCl)). The neutralized cell suspension was washed with water by centrifugation. The cell suspension was dried and yielded a product containing a very low level of purine bases.

EXAMPLE II

The process of Example I was repeated except that prior to drying the cell suspension, it was combined with the water extract (Extract-1) to give a reconstituted product. Yields and the purine content in various fractions are shown in Table II.A.

EXAMPLE III

The process of Example I was repeated except that a solution of methionine at a dosage of 1.2% of the dried cell product was added to the cell suspension of low purine containing cell material before it was spray dried.

Samples of both methionine enriched products and non-methionine enriched products were tested for Protein Efficiency Ratio (PER). The results of the tests are shown in Table I.A.

TABLE I.A

| Sample | Methionine content g/16 g. nitrogen | PER |
|---|---|---|
| Regular torula yeast | 1.4 | 1.88 |
| Low-purine yeast cell | 1.6 | 1.58 |
| Methionine enriched low-purine cell | 3.9 | 2.34 |

TABLE II.A

Composition of Purines (Adenine & Guanine) in Various Fractions of Alkaline Extracted Yeast Products[1]

| Fractions and Products | Yield of Dry Wt. gm | Adenine gm | Guanine gm | Purines (A + G)[3] gm | Purines Content % | A/G | Daily Intake Limit of Product, gm[2] |
|---|---|---|---|---|---|---|---|
| (1) Untreated Cells | 100 | 0.87 | 1.00 | 1.87 | 1.87 | 0.87 | 19 |
| (2) Water Extract (EX-1) | 18 | 0.23 | 0.14 | 0.37 | 2.06 | 1.64 | — |
| (3) Alkaline Extract (EX-2) | 10 | 0.56 | 0.74 | 1.30 | 13.00 | 0.76 | — |
| (4) Low-Purine Cell | 72 | 0.08 | 0.12 | 0.20 | 0.28 | 0.67 | 129 |
| (5) Reconstituted Cell (2) + (4) | 90 | 0.31 | 0.26 | 0.57 | 0.63 | 1.20 | 57 |

[1]Purine composition is determined by paper chromatographic analysis after the samples are hydrolyzed by 1 normal HCl at 100°C for 1 hour.
[2]Based on a daily limit of 2 grams of yeast RNA, or 0.36 grams of purine bases.
[3]"A" represents Adenine and "G" represents Guanine.

I claim:

1. A process for substantially reducing the purine content while increasing the yield and nutritive value of single-cell protein material, intended for use in food products and derived from unicellular microorganisms grown in a fermentor aerobically in a suitable fermentation broth, comprising the steps of:
   a. preparing an aqueous cell cream containing from 10 to 14 wt.% (dry basis) of single-cell protein material;
   b. heating the cell cream to a temperature within the range from about 70° to about 90°C. for a period of about 5 to about 10 minutes;
   c. centrifuging the heated cell cream to provide (1) a supernatant aqueous phase and (2) a heat-treated cell concentrate;
   d. adding water to the heat-treated cell concentrate from step (c) (2) to provide an aqueous cell cream containing from 10 to 14 wt.% (dry basis) of single-cell protein material;
   e. maintaining the pH of the aqueous cell cream provided in step (d) at a pH of about 8.5 to about 10.0 by adding a base solution as needed, and heating the cell cream to a temperature within the range from about 85° to 95°C. for a period of about 5 to about 30 minutes;
   f. centrifuging the aqueous cell cream of step (e) to provide (1) a supernatant and (2) a treated cell concentrate, having substantially reduced purine content;
   g. adjusting the pH of the cell concentrate provided in step (f)(2) to about 7.0 by adding hydrochloric acid;
   h. washing the pH adjusted cell concentrate of step (g) with water by centrifugation;
   i. combining (1) the water-washed heat-treated cell concentrate produced in step (h) with (2) the supernatant aqueous phase produced in step (c)(1); and
   j. drying the mixture of step (i) to give a reconstituted product.

2. The process of claim 1 wherein:
   a. the supernatant aqueous phase provided in step (c)(1) is subjected to fractionation to provide (1) a purine depleted fraction and (2) a purine concentrated fraction;
b. the water-washed heat-treated cell concentrate produced in step (h) is combined with the purine depleted fraction produced in step (a)(1); and
c. the mixture of step (b) is dried to give a reconstituted product.

3. The process of claim 2 wherein the combined mixture of step (b) is fortified with an amino acid selected from the group consisting essentially of methionine and cystine.

4. The process of claim 1 wherein the base solution in step (e) is selected from the group consisting of ammonium hydroxide, sodium hydroxide and sodium carbonate.

5. The process of claim 1 wherein the cell cream comprises about 10 wt.% cells.

6. The process of claim 1 wherein the unicellular microorganism is a bacteria, yeast or fungi.

7. The process of claim 6 wherein the unicellular microorganism is a yeast.

8. The process of claim 7 wherein the unicellular microorganism is a yeast selected from the class consisting of *Saccharomyces cerevisiae*, *Saccharomyces carlsbergensis*, *Saccharomyces fragilis* and *Candida utilis*.

9. The process of claim 8 wherein the yeast is *Candida utilis*.

10. The process of claim 1 wherein the combined product of step (i) is fortified with amino acids selected from the group consisting essentially of methionine and cystine.

11. The process of claim 10 wherein the base solution in step (e) is selected from the group consisting of ammonium hydroxide, sodium hydroxide and sodium carbonate.

12. The process of claim 11 wherein the unicellular microorganism is a yeast.

13. The process of claim 12 wherein the yeast is selected from the class consisting of *Saccharomyces cerevisiae*, *Saccharomyces carlsbergensis*, *Saccharomyces fragilis* and *Candida utilis*.

14. The process of claim 13 wherein the yeast is *Candida utilis*.

15. The product prepared by the process of claim 1.
16. The product prepared by the process of claim 2.
17. The product prepared by the process of claim 3.
18. The product prepared by the process of claim 10.

* * * * *